US005666427A

United States Patent [19]

Kim et al.

[11] Patent Number: 5,666,427

[45] Date of Patent: Sep. 9, 1997

[54] METHOD OF AND APPARATUS FOR CONTROLLING NOISE GENERATED IN CONFINED SPACES

[75] Inventors: Won Young Kim, Changwon; Yang Han Kim; Seong Woo Kang, both of Taejon, all of Rep. of Korea

[73] Assignee: Samsung Heavy Industries Co. Ltd., Seoul, Rep. of Korea

[21] Appl. No.: 564,827

[22] Filed: Nov. 29, 1995

[30] Foreign Application Priority Data

Sep. 30, 1995 [KR] Rep. of Korea ..................... 95-33514
Sep. 30, 1995 [KR] Rep. of Korea ..................... 95-335516

[51] Int. Cl.[6] ............................ A61F 11/06; H03B 29/00

[52] U.S. Cl. ......................... 381/71.1; 381/72; 381/94.1; 381/96

[58] Field of Search ............................... 381/71, 94, 72, 381/96

[56] References Cited

U.S. PATENT DOCUMENTS 2,736,711 2/1956 Hanson et al. ........................... 381/71
4,562,589 12/1985 Warnaka et al. .......................... 381/71

FOREIGN PATENT DOCUMENTS 8400274 1/1984 WIPO ...................................... 381/96

*Primary Examiner*—Curtis Kuntz
*Assistant Examiner*—Duc Nguyen
*Attorney, Agent, or Firm*—Kenyon & Kenyon

[57] ABSTRACT

A method of and an apparatus for controlling noise generated in a confined space, being capable of reducing a radiating sound pressure generated from a main noise source to that of an optimal state. The method includes the steps of measuring the radiating sound pressure generated from the noise source, and generating, from an additional sound source, a radiating sound pressure having the same magnitude as the radiating sound pressure generated from the noise source while having a phase 180°-shifted from that of the noise source's radiating sound pressure so that the radiating sound pressures can offset each other when they are mixed. The apparatus includes an additional sound source installed in the confined space, an intensity converter for collecting and measuring sound pressure signals respectively generated from the noise source and the additional sound source, and a microcomputer for applying, to the additional sound source, a control signal for reducing the noise on the basis of the sound pressure signals measured by the intensity converter.

5 Claims, 2 Drawing Sheets

METHOD OF AND APPARATUS FOR CONTROLLING NOISE GENERATED IN CONFINED SPACES

BACKGROUND OF THE INVENTION

1. Field of the Invention

The present invention relates to a method of and an apparatus for controlling noise generated in a confined space, and a method of and an apparatus for controlling noise generated in a confined space, being capable of reducing a radiating sound pressure (including vector components) generated from a main noise source to that of an optimal state.

2. Description of the Prior Art

Generally, noise generated from mechanical devices which are operated inside or outside of confined spaces such as cabs, ship's cabins, vehicle interiors or office rooms is the factor for causing workers in the confined spaces to be uncomfortable. Such noise also results in a degradation in work efficiency. To this end, a variety of noise reducing techniques have been proposed.

Among known noise reducing techniques, One relatively efficient method is a system using an additional sound source (for example, a speaker) adapted to interfere with a noise source in phase, thereby being capable of obtaining a noise offset effect. In this connection, much researches in positive noise control techniques have been actively made. This technique is efficiently applicable even to a frequency band noise where it is difficult to expect a noise reducing effect by using only a sound absorbing material or sound shielding material (for example, a low frequency band of about 500 Hz). Among systems using this technique, the generally known one Is the system wherein a sensor is attached to a desired area in a confined space where noise is problematic (for example, the driver's seat in a cab). The sensor serves to drive the additional sound source In order to minimize noise at the desired area.

However, the positive noise reduction technique has many problems as follows.

First, although the noise reduction effect is obtained at the area, where the sensor Is installed, by virtue of a noise offset effect generated at the area, the generation of noise may rather be increased at other areas because no noise offset effect is generated at those areas.

Second, where it is desired to obtain the noise reduction effect in a large space, it is necessary to install a plurality of sensors respectively at a plurality of areas in the space, thereby performing a multi-channel signal processing. In this case, a complex control should be performed so as to accurately execute the multi-channel signal processing. However, such a complex control requires a high-speed, large discrete signal processing unit. As a result, the overall system is expensive. Furthermore, this system has a degraded performance, resulting In a degraded utility.

Third, it is actually difficult to determine an optimal installation position of the sensor. For example, although the sensor is attached to the head support of the driver's seat in the interior of the cab, it can not provide an optimum noise reduction effect when the driver moves from his seat to another position during the operation of the mechanical device.

SUMMARY OF THE INVENTION

Therefore, an object of the invention is to solve the above-mentioned problems and to provide a method for controlling noise generated in a confined space, being capable of achieving the same noise reduction effect at any area in the confined space.

Another object of the invention is to provide a method for controlling noise generated in a confined space, being capable of precisely measuring the radiating sound pressure, or acoustic power, generated from an additional sound source to minimize a radiating sound pressure generated from a main noise source, thereby obtaining an optimum noise reduction effect.

Another object of the invention is to provide a method for controlling noise generated in a confined space, being capable of determining the position of an additional sound source to reduce a radiating sound pressure generated from a main noise source to that of an optimal state, thereby obtaining an optimum noise reduction effect.

Still another object of the invention is to provide an apparatus for controlling noise generated in a confined space, being capable of accomplishing the above-mentioned objects.

In accordance with one aspect, the present invention provides a method for controlling noise In a confined space to reduce a radiating sound pressure generated from at least one noise source, comprising the steps of: measuring the radiating sound pressure generated from the noise source; and generating, from an additional sound source, a radiating sound pressure having the same magnitude as the radiating sound pressure generated from the noise source while having a phase 180°-shifted from that of the noise source's radiating sound pressure so that the radiating sound pressures can offset each other when they are mixed.

In this case, it is preferred that the generation of the radiating sound pressure, or acoustic power, from the additional sound source is achieved by detecting a vibration velocity signal and a sound pressure signal at the front of the additional sound source, and then adding the sound pressure signal to the vibration velocity signal, thereby detecting a final vibration velocity, phase-shifting the sound pressure signal and then adding the phase-shifted sound pressure signal to the vibration velocity signal, thereby detecting a final sound pressure, measuring the radiating sound pressure generated from the additional sound source en the basis of the detected final vibration velocity and final sound pressure, and minutely adjusting the radiating sound pressure being generated from the additional sound source to reduce the radiating sound pressure generated from the noise sound source to a minimum value when the radiating sound pressure of the additional sound source is mixed with the radiating sound pressure of the noise source.

In accordance with another aspect, the present invention provides a method for controlling noise in a confined space to reduce a radiating sound pressure generated from at least one noise source, comprising the steps of measuring the radiating sound pressure generated from the noise source, generating, from an additional sound source, a radiating sound pressure having the same magnitude as the radiating sound pressure generated from the noise source while having a phase 180°-shifted from that of the noise source's radiating sound pressure, and determining an optimal position of the additional sound source so that the radiating sound pressures can offset each other when they are mixed.

In this case, it is preferred that the generation of the radiating sound pressure, or acoustic power, from the additional sound source is achieved by detecting a vibration velocity signal and a sound pressure signal at the front of the additional sound source, and then adding the sound pressure signal to the vibration velocity signal, thereby detecting a final vibration velocity, phase-shifting the sound pressure signal and then adding the phase-shifted sound pressure signal to the vibration velocity signal, thereby detecting a final sound pressure, measuring the radiating sound pressure generated from the additional sound source on the basis of the detected final vibration velocity and final sound pressure, and minutely adjusting the radiating sound pressure being generated from the additional sound source to reduce the radiating sound pressure generated from the noise sound source to a minimum value when the radiating sound pressure of the additional sound source is mixed with the radiating sound pressure of the noise source.

Preferably, the optimal position of the additional sound source is determined by calculating a vibration velocity and a sound pressure both generated from the noise source and a vibration velocity and a sound pressure both generated from the additional sound source, deriving the following position determining function on the basis of the calculated vibration velocities and sound pressures, and determining, as the optimal position, a position of the additional sound source where the position determining function approximates to 1.

$$\{N_{ps}^2(f)\}^2 = \frac{Re\,(H_{V_sP_p})^2}{Re\{H_{V_pP_p}(f)\} \times Re\{H_{V_sP_s}(f)\}}$$

where, $N_{ps}^2(f)$: Position determining function;

$Re(H_{V_pP_p})$: Real number part transfer function based on the vibration velocity Vp and sound pressure Pp from the engine 3;

$Re(H_{V_sP_s})$: Real number part transfer function based on the vibration velocity Vs and sound pressure Ps from the speaker 1;

$Re(H_{V_sP_p})$: Real number part transfer function based on the vibration velocity Vs from the speaker 1 and the sound pressure Pp from the engine 3;

Vp, Vs: Respective vibration velocities of the engine and speaker 1; and

Pp, Ps: Respective sound pressures of the engine 3 and speaker 1.

In accordance with another aspect, the present invention provides an apparatus for controlling noise in a confined space having at least One noise source, comprising: an additional sound source installed in the confined space; an intensity converter for collecting and measuring sound pressure signals respectively generated from the noise source and the additional sound source; and a microcomputer for applying, to the additional sound source, a control signal for reducing the noise on the basis of the sound pressure signals measured by the intensity converter.

The apparatus further comprises a first microphone mounted such that it is disposed at a plane extending along a front end of the additional sound source, the first microphone serving to detect a vibration velocity signal generated from the additional sound source, and a second microphone mounted at a position spaced a certain distance apart forward from the plane where the first microphone is mounted, the second microphone serving to detect the sound pressure generated from the additional sound source.

The intensity converter comprises a first adder for adding the sound pressure signal detected by the second microphone to the vibration velocity signal detected by the first microphone, thereby outputting a final vibration velocity signal, a second adder for phase shifting the sound pressure signal detected by the second microphone and then adding the phase-shifted sound pressure signal to the vibration velocity signal detected by the first microphone; and an integrator for integrating the result by the addition from the second adder, thereby outputting a final sound pressure.

The apparatus further comprises pre-amplifiers respectively adapted to amplify various signals detected by the first and second microphones to magnitudes appropriate to their processing.

The apparatus further comprises low-pass filters respectively adapted to prevent output signals from the intensity converter from being deformed when they are processed.

The additional sound source is a speaker.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 1:
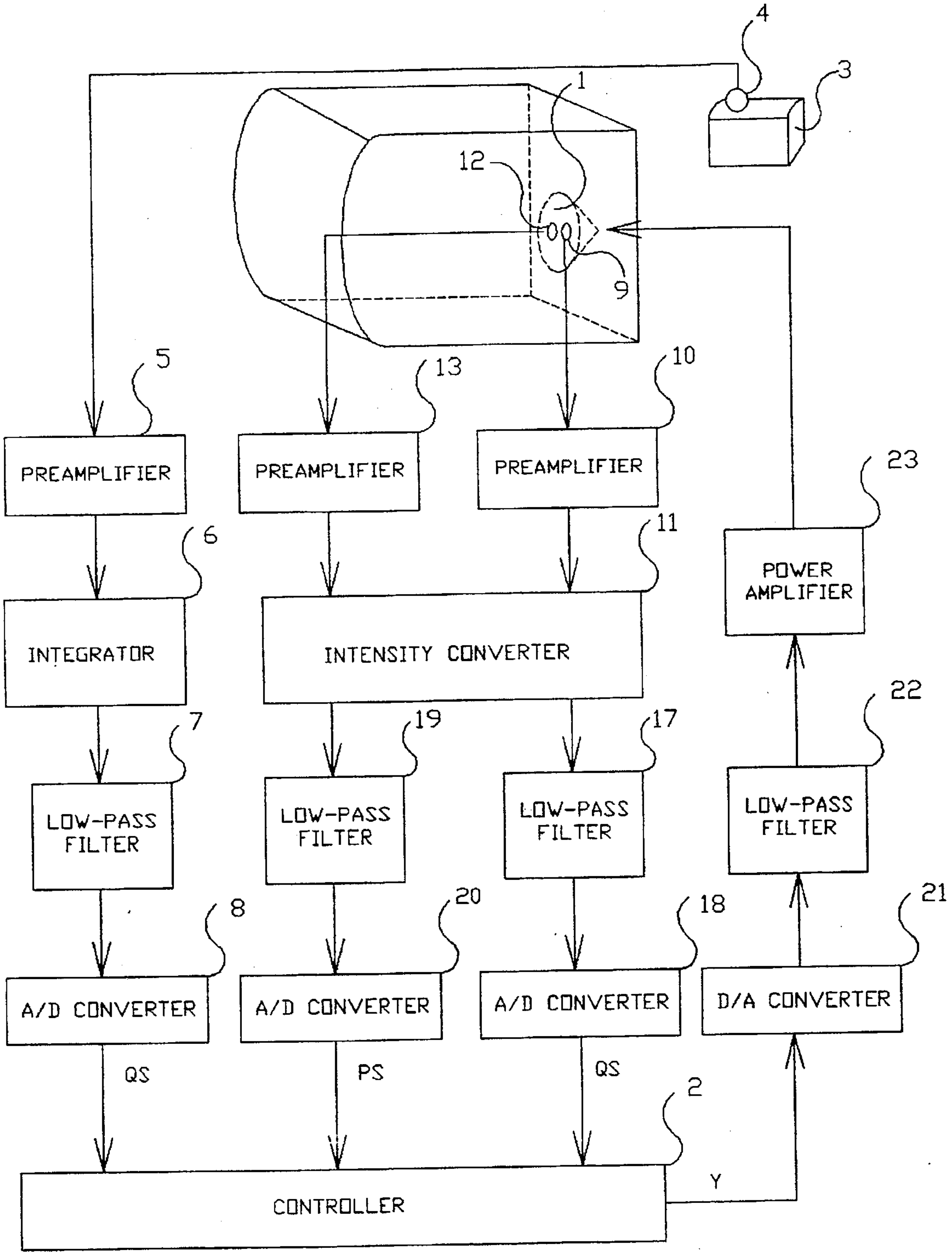
FIG. 1 is a block diagram illustrating an apparatus for controlling noise generated in a confined space in accordance with the present invention.

FIG. 1 is a block diagram illustrating an apparatus for controlling noise generated in a confined space in accordance with the present invention. Although the present invention will be described as being applied to construction equipment, it should be noted that the invention is applicable to other kinds of noise environments.

The basic principle of the present invention will be first described. In accordance with the present invention, the magnitude and vector component of a radiating sound pressure, or acoustic power, generated from a main noise source is calculated. Based on the calculated magnitude and vector component of the radiating sound pressure, an additional, radiating sound pressure, or acoustic power, is generated which has the same magnitude as the radiating sound pressure generated from the main noise source while having a vector component with a phase difference of 180° from the main noise source's radiating sound pressure. By virtue of the phase difference, these two radiating sound pressures offset each other, so that they will disappear.

In this case, it is very important to control the radiating sound pressure generated from the additional sound source such that it has the same magnitude as the radiating sound pressure generated from the main noise source while having vector components with a phase difference of 180° from the main noise source's radiating sound pressure.

For obtaining an optimum noise control performance, it is necessary to precisely measure the magnitude and phase of the radiating sound pressure generated from the additional sound source and to control the position of the additional sound source such that the radiating sound pressure generated from the additional sound source has a phase 180°-shifted from the phase of the radiating sound pressure generated from the main noise source.

In accordance with the above-mentioned principle of the present invention, the apparatus of FIG. 1 includes an additional sound source 1 installed in a cab. The additional sound source may be a speaker. The apparatus also includes a controller 2 for collecting a signal generated from a main noise source, a sound pressure signal generated from the speaker 1 and detected at the front of the speaker 1 and a vibration velocity signal generated from the speaker 1 and detected at the front of the speaker 1. The controller 2 generates a control signal for reducing noise generated from the main noise source on the basis of the collected signals.

In order to collect a variety of signals as mentioned above, the apparatus also Includes pre-amplifiers 5, 10 and 13. The pre-amplifier 5 receives an acceleration signal generated from an acceleration meter 4 serving to measure the accelerated rotation velocity of an engine 3 which is the main noise source and amplifies the received signal. The amplified signal from the pre-amplifier 5 is received to an integrator 6 which serves to integrate the received signal, thereby converting it Into a continuous velocity signal. This continuous velocity signal from the integrator 6 is received to a low-pass filter 7 which serves to filter the received signal in order to output low frequency components of the signal. The resultant signal from the low-pass filter 7 Is sent to an analog/digital (A/D) converter 8 which converts the received signal into a digital signal having the same form as the vibration velocity signal Qp of the main noise source, namely, the engine 3. The digital signal from the A/D converter 8 is applied to the controller 2. Thus, collecting the signal from the engine 3 is completed. The low-pass filter 7 Is used to prevent an aliasing phenomenon occurring when the continuous velocity signal is converted into the digital signal in the A/D converter 8.

On the other hand, the apparatus also includes a first microphone 9 mounted such that it is disposed at a plane extending along the front end of the speaker 1. The vibration velocity signal at the front of the speaker 1 is detected by the first microphone 9 which, in turn, sends the detected signal to an intensity converter 11 via the pre-amplifier 10.

The apparatus also includes a second microphone 12 mounted at a position spaced a certain distance apart forward from the plane where the first microphone 9 is mounted. The sound pressure signal at the front of the speaker 1, which includes no vector component as different from radiating sound pressure, or acoustic power, is detected by the second microphone 12 which, in turn, sends the detected signal to the intensity converter 11 via the pre-amplifier 13.

Figure 2:
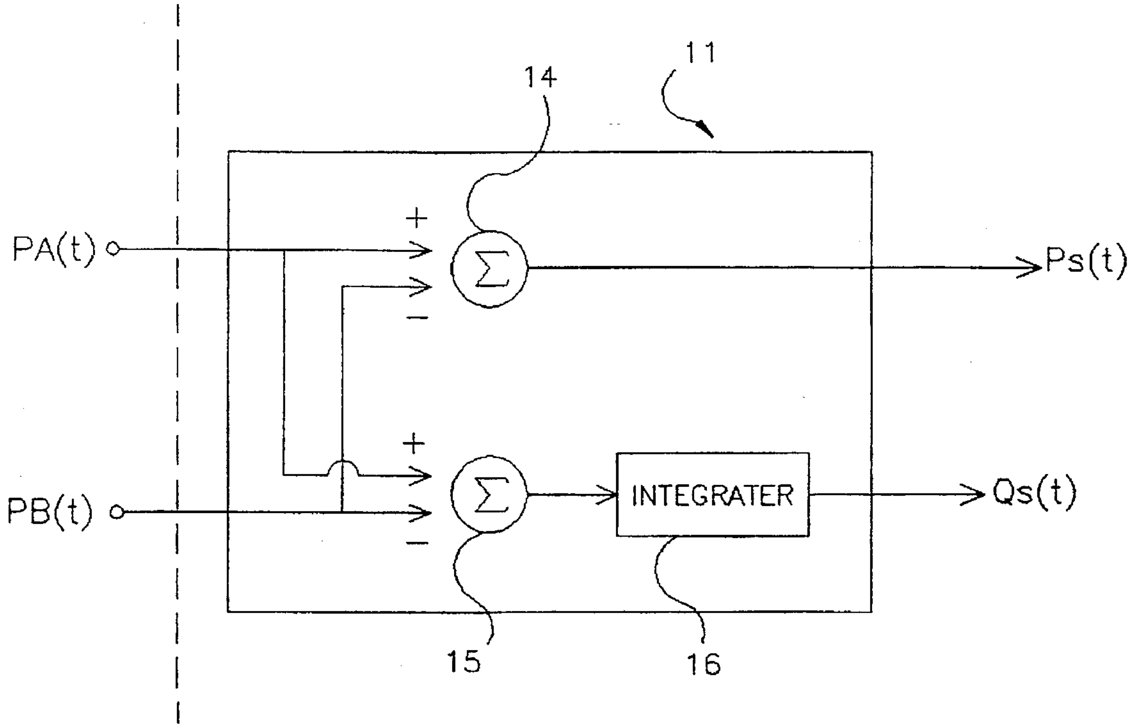
FIG. 2 is a block diagram illustrating an intensity converter included in the apparatus of FIG. 1.

As shown in FIG. 2, the Intensity converter 11 includes a first adder 14 for adding the sound pressure signal detected by the second microphone 12 to the vibration velocity signal detected by the first microphone 9, thereby outputting the resultant signal as a final vibration velocity signal Qs. The intensity converter 11 further includes a second adder 14 for phase shifting the sound pressure signal detected by the second microphone 12 and then adding the phase-shifted sound pressure signal to the vibration velocity signal detected by the first microphone 9. An integrator 16 is also provided which serves to integrate the result by the addition from the second adder 15, thereby outputting a final sound pressure Ps.

In other words, the intensity converter 11 outputs the vibration velocity signal Qs which is detected in terms of the vibration velocity and phase on the basis of the two input signals, namely, the vibration velocity signal detected by the first microphone 9 and the sound pressure signal detected by the second microphone 12. The vibration velocity signal Qs from the intensity converter 11 is then applied to the controller 2 via the low-pass filter 17 and A/D converter 18.

The intensity converter 11 also calculates the sound pressure Ps output from the speaker 1 using the two input signals, namely, the vibration velocity signal detected by the first microphone 9 and the sound pressure signal detected by the second microphone 12. The sound pressure signal Ps output from the intensity converter 11 is then applied to the controller 2 via the low-pass filter 19 and A/D converter 20.

The controller 2 calculates a radiating sound pressure, or acoustic power, using the two input signals, namely, the vibration velocity Qs and sound pressure Ps detected at the front of the speaker 1. Since the radiating sound pressure, or acoutic power, corresponds to the product of the vibration velocity Qs by the sound pressure Ps, it can be expressed by "Qs×Ps".

After calculating the radiating sound pressure, or acoustic power, the controller 2 compares the calculated radiating sound pressure with the radiating sound pressure generated from the engine 3 in order to check whether the two radiating sound pressures offset each other when they are mixed so that the mixed radiating sound pressure can be minimized. On the basis of the checked result, the controller 2 then minutely varies the value of its control signal Y until the mixed radiating sound pressure is minimized.

The control signal Y from the controller 2 is sent to a digital/analog (D/A) converter 21 which, in turn, converts the signal into a digital signal. The control signal from the D/A converter 21 is sent to the speaker 1 via a low-pass filter 22 and a power amplifier 23. In accordance with the control signal, the speaker 1 generates a radiating sound pressure which is minutely varied from the initially output radiating sound pressure. In such a manner, it is possible to detect the radiating sound pressure from the speaker 1 which is capable of minimizing the radiating sound pressure generated from the engine 3.

On the other hand, it is very desirable to detect the optimal position of the additional sound source, namely, the speaker 1 so as to enhance the effect obtained by the method for controlling noise in a confined space in accordance with the present invention.

To this end, the intensity converter 11 also outputs *a vibration velocity signal Vs which is detected in terms of the vibration velocity and phase on the basis of the two input signals, namely, the vibration velocity signal detected by the first microphone 9 and the sound pressure signal detected by the second microphone 12. The vibration velocity signal Vs from the intensity converter 11 is then applied to the controller 2 via the low-pass filter 17 and A/D converter 18.

In this case, the intensity converter 11 also calculates the sound pressure Ps output from the speaker 1 using the two input signals, namely, the vibration velocity signal detected by the first microphone 9 and the sound pressure signal detected by the second microphone 12. The sound pressure signal Ps output from the intensity converter 11 is then applied to the controller 2 via the low-pass filter 19 and A/D converter 20.

On the basis of the vibration velocity Qp and sound pressure Pp of the main noise source, namely, the engine 3 and the vibration velocity Vs and sound pressure Ps of the speaker 1, the controller 2 then derives a position determining function for determining the optimal position of the speaker 1. The position determining function is expressed by the following equation (1):

$$\{N_{ps}^2(f)\}^2 = \frac{Re\,(HVsPp)^2}{Re\{H_{VpPp}(f)\} \times Re\{H_{VsPs}(f)\}} \tag{1}$$

where, $N_{ps}{}^2(f)$: Position determining function;

$Re(H_{VpPp})$: Real number part transfer function based on the vibration velocity Vp and sound pressure Pp from the engine 3;

$Re(H_{VsPs})$: Real number part transfer function based on the vibration velocity Vs and sound pressure Ps from the speaker 1;

$Re(H_{VsPp})$: Real number part transfer function based on the vibration velocity Vs from the speaker 1 and the sound pressure Pp from the engine 3;

Vp, Vs: Respective vibration velocities of the engine 3 and speaker 1; and Pp, Ps: Respective sound pressures of the engine 3 and speaker 1.

The position determining function expressed by the equation (1) always satisfies the following inequality (2):

$$0<N_{ps}^2(f)\leq 1 \qquad (2)$$

This means that the above position determining function is an acoustical interactive coupling function between the main noise source and the additional sound source. When the vibration velocity Vp and sound pressure Pp of the engine 3 have the same values as the vibration velocity Vs and the sound pressure Ps of the speaker 1, respectively, the position determining function becomes 1. Accordingly, it is possible to reduce noise to that of an optimal state by finding a speaker mounting position where the position determining function approximates to 1 and mounting the speaker 1 to the speaker mounting position.

Thereafter, the controller 2 outputs a control signal Y so that the speaker 1 can output a radiating sound pressure having a phase 180°-shifted from that of the radiating sound pressure generated from the engine 3. The control signal Y from the controller 2 is converted into a digital signal by the D/A converter 21 which, in turn, sends the control signal to the speaker 1 via the low-pass filter 22 and power amplifier 23. Based on the control signal, the speaker 1 generates a radiating sound pressure capable of minimizing the radiating sound pressure generated from the engine 3.

As apparent from the above description, the present invention provides a method of and an apparatus for controlling noise generated In a confined space, capable of providing an additional sound source which can generate a radiating sound pressure serving to reduce a radiating sound pressure generated from a main noise source to that of an optimal state. Accordingly, it is possible to obtain the same noise reduction effect at any area in a confined space.

In accordance with the present invention, the radiating sound pressure generated from the additional sound source can be precisely measured. Accordingly, the additional sound source can generate a radiating sound pressure capable of minimizing the radiating sound pressure generated from the main noise source, thereby efficiently reducing the main noise source's sound pressure.

Moreover, the radiating sound pressure of the additional sound source can be minutely adjusted to minimize the radiating sound pressure generated from the main noise source in accordance with the present invention. Accordingly, there is an advantage of more efficiently reducing the radiating sound pressure of the main noise source.

In addition, an optimal position of the additional sound source capable of minimizing the radiating sound pressure of the main noise source can be accurately determined in accordance with the present invention. Accordingly, the present invention provides an advantage of reducing the radiating sound pressure of the main noise source to that of an optimal state.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for controlling noise in a confined space to reduce a first acoustic power generated from at least one noise source, comprising the steps of:

measuring the first acoustic power generated from the noise source; and generating, from an additional sound source, a second acoustic power having the same magnitude as the first acoustic power generated from the noise source while having a phase 180°-shifted from that of the noise source's first acoustic power so that the first and second acoustic powers can offset each other when they are mixed;

wherein the step of generating the second acoustic power from the additional sound source comprises:

detecting a vibration velocity signal and a sound pressure signal at the front of the additional sound source, and then adding the sound pressure signal to the vibration velocity signal, thereby detecting a final vibration velocity;

phase-shifting the sound pressure signal and then adding the phase-shifted sound pressure signal to the vibration velocity signal, thereby detecting a final sound pressure;

measuring the second acoustic power generated from the additional sound source on the basis of the detected final vibration velocity and final sound pressure; and minutely adjusting the second acoustic power being generated from the additional sound source to reduce the first acoustic power generated from the noise sound source to a minimum value when the second acoustic power of the additional sound source is mixed with the first acoustic power of the noise source.

2. A method for controlling noise in a confined space to reduce a first acoustic power generated from at least one noise source, comprising the steps of:

measuring the first acoustic power generated from the noise source, generating, from an additional sound source, a second acoustic power having the same magnitude as the first acoustic power generated from the noise source while having a phase 180°-shifted from that of the noise source's first acoustic power, and determining an optimal position of the additional sound source so that the first and second acoustic powers can offset each other when they are mixed, wherein the step of generating the second acoustic power from the additional sound source comprises:

detecting a vibration velocity signal and a sound pressure signal at the front of the additional sound source, and then adding the sound pressure signal to the vibration velocity signal, thereby detecting a final vibration velocity;

phase-shifting the sound pressure signal and then adding the phase-shifted sound pressure signal to the vibration velocity signal, thereby detecting a final sound pressure;

measuring the second acoustic power generated from the additional sound source on the basis of the detected final vibration velocity and final sound pressure; and minutely adjusting the second acoustic power being generated from the additional sound source to reduce the first acoustic power generated from the noise sound source to a minimum value when the second acoustic power of the additional sound source is mixed with the first acoustic power of the noise source.

3. A method for controlling noise in a confined space to reduce a first acoustic power generated from at least one noise source, comprising the steps of:

measuring the first acoustic power generated from the noise source, generating, from an additional sound source, a second acoustic power having the same magnitude as the first acoustic power generated from the noise source while having a phase 180°-shifted from that of the noise source's first acoustic power, and determining an optimal position of the additional sound source so that the first and second acoustic powers can offset each other when they are mixed, wherein the step of measuring the optimal position of the additional sound source comprises:

calculating a vibration velocity and a sound pressure both generated from the noise source and a vibration velocity and a sound pressure both generated from the additional sound source;

deriving the following position determining function on the basis of the calculated vibration velocities and sound pressures; and determining, as the optimal position, a position of the additional sound source where the position determining function approximates to 1; wherein $$(N_{ps}^2(f))^2 = \frac{Re\,(H_{V_sP_p})^2}{Re(H_{V_pP_p}(f)) \times Re(H_{V_sP_s}(f))}$$

where, $N_{ps}^2(f)$ is a position determining function;

$Re(H_{V_pP_p})$ is a real number part transfer function based on the vibration velocity Vp and sound pressure Pp from the engine 3;

$Re(H_{V_sP_s})$ is a real number part transfer function based on the vibration velocity Vs and sound pressure Ps from the speaker 1;

$Re(H_{V_sP_p})$ is a real number part transfer function based on the vibration velocity Vs from the speaker 1 and the sound pressure Pp from the engine 3;

Vp and Vs are respective vibration velocities of the engine 3 and speaker 1; and Pp and Ps are respective sound pressures of the engine 3 and speaker 1.

4. An apparatus for controlling noise in a confined space having at least one noise source, comprising:

an additional sound source installed in the confined space;

an intensity converter for collecting and measuring sound pressure signals respectively generated from the noise source and the additional sound source; and a microcomputer for applying to the additional sound source, a control signal for reducing the noise on the basis of the sound pressure signals measured by the intensity converter;

wherein the intensity converter comprises:

a first adder for adding the sound pressure signal detected by the second microphone to the vibration velocity signal detected by the first microphone, thereby outputting a final vibration velocity signal;

a second adder for phase shifting the sound pressure signal detected by the second microphone and then adding the phase-shifted sound pressure signal to the vibration velocity signal detected by the first microphone; and an integrator for integrating the result by the addition from the second adder, thereby outputting a final sound pressure.

5. The apparatus in accordance with claim 4, further comprising:

low-pass filters respectively adapted to prevent output signals from the intensity converter from being deformed when they are processed.

* * * * *